(12) United States Patent
Abraham et al.

(10) Patent No.: US 8,591,703 B2
(45) Date of Patent: *Nov. 26, 2013

(54) MONOFILAMENT YARN FOR A PAPER MACHINE CLOTHING FABRIC

(75) Inventors: Jürgen Abraham, Nattheim (DE); Ashish Sen, Summerville, SC (US); Brian Good, Summerville, SC (US)

(73) Assignee: Voith Patent GmbH, Heidenheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/177,082

(22) Filed: Jul. 6, 2011

(65) Prior Publication Data

US 2013/0008622 A1    Jan. 10, 2013

(51) Int. Cl.
*D21F 3/00*    (2006.01)

(52) U.S. Cl.
USPC ...................................... 162/358.2

(58) Field of Classification Search
USPC .............. 162/358.2, 348, 289, 199, 900–904, 162/361, 362; 442/189, 199; 264/210.8; 428/401
See application file for complete search history.

(56) References Cited

U.S. PATENT DOCUMENTS

| | | | | |
|---|---|---|---|---|
| 4,212,763 A | * | 7/1980 | Fringeli | 252/301.23 |
| 6,827,821 B2 | * | 12/2004 | Brewster et al. | 162/358.2 |
| 7,897,018 B2 | * | 3/2011 | O'Connor et al. | 162/348 |
| 2003/0226611 A1 | | 12/2003 | Moriarty et al. | |
| 2006/0019093 A1 | * | 1/2006 | Zhang et al. | 428/364 |
| 2007/0028997 A1 | * | 2/2007 | Best et al. | 139/383 R |

FOREIGN PATENT DOCUMENTS

GB    2 316 354 A    2/1998

OTHER PUBLICATIONS

International Search Report and Written Opinion dated Oct. 16, 2012 for International Application No. PCT/EP2012/062979 (11 pages).

* cited by examiner

*Primary Examiner* — Mark Halpern
(74) *Attorney, Agent, or Firm* — Taylor IP, P.C.

(57) ABSTRACT

A paper machine clothing (PMC) fabric including a plurality of monofilament yarns, at least some of the monofilament yarns having a composition which includes an additive for detecting a defect on the paper machine clothing fabric.

14 Claims, 4 Drawing Sheets

MONOFILAMENT YARN FOR A PAPER MACHINE CLOTHING FABRIC

BACKGROUND OF THE INVENTION

1. Field of the Invention

The present invention relates to a paper machine clothing, and more particularly, to the composition of monofilaments used in the paper machine clothing.

2. Description of the Related Art

A paper machine clothing (PMC) fabric is typically manufactured with a specific set of design and quality specifications for a particular paper machine's performance requirements. These specifications include surface characteristics, open area, void volume, permeability and smoothness, among others. The need to implement an effective PMC fabric cleaning and inspection program is crucial to newer, faster machines, higher quality requirements and the desire for extended fabric life.

All fabrics, especially dryer fabrics, should be periodically cleaned and inspected so that their original properties are retained as long as possible and their value is optimized. The fabric of the paper machine clothing must be cleaned in order to maintain the required permeability and to prevent sheet streaking due to non-uniform dewatering and drying profiles, sheet drop-offs in vacuum assisted transfers, uniruns and single dryer runs. Fabric cleaning is accomplished both mechanically, for example by showering, and chemically. Some of the more common consequences resulting from fabric contamination are, for example, sheet moisture profile unevenness, sheet instability and the transfer of deposits from the fabric to the paper. In addition, dryer fabric contamination can lead to issues related to non-uniform heat transfer, reduced heat transfer resulting from deposits left on the drying cylinders, and plugged vacuum rolls.

What is needed in the art is a PMC fabric which allows for effective monitoring of the cleanliness and overall condition of a fabric.

SUMMARY OF THE INVENTION

The present invention provides a PMC fabric which may be effectively cleaned and efficiently inspected or examined for defects or contamination and, further to a method of making and inspecting the PMC fabric. More specifically, the present invention provides a PMC fabric including a plurality of monofilament yarns, at least some of which have a composition including an additive for detecting a defect on the PMC fabric using a light or radiation source. The additive may, for example, be an ultraviolet (UV) additive, an infrared (IR) additive or a metallic powder additive. The UV additive may be a stilbene, for example 4,4'-bis(benzoxazol) stilbene.

The present invention further provides a PMC fabric yarn for a PMC fabric. At least some of the monofilament yarns have a composition including between approximately 100 and 10,000 parts per million (ppm), for example 1,000 ppm, of an additive such as an ultraviolet (UV) additive for detecting a defect on the PMC fabric using short wavelength radiation at a wavelength of between approximately 300 nanometers (nm) to 400 nm.

The present invention further provides a PMC fabric yarn for a PMC fabric. The PMC yarn has a composition which includes between approximately 100 and 10,000 ppm of a UV additive for detecting a defect, contaminant or imperfection on the PMC fabric using short wavelength radiation at a wavelength of between approximately 300 nm to 400 nm.

The invention in another form is directed to a method of manufacturing a PMC fabric yarn including the steps of melt blending a mixture of an additive and a thermoplastic resin, spinning the mixture into a filament and drawing the filament into a monofilament PMC fabric yarn. The method further includes the step of then using a light source to increase visibility of the PMC fabric yarn and detect a defect in the PMC fabric yarn. The additive is, for example, a UV additive, an IR additive or a metal powder additive. The composition includes, for example, between 100 and 10,000 ppm of the additive.

The invention in another form is directed to a method of inspecting a PMC fabric including the steps of providing a PMC fabric including monofilament yarns, at least some of which include between approximately 100 and 10,000 ppm of a UV additive, and then using short wavelength radiation at a wavelength of between approximately 300 nm and 400 nm to detect a defect on the PMC fabric.

The present invention further provides a method of manufacturing a PMC fabric yarn including the steps of spinning a thermoplastic resin into a filament, drawing the filament into a monofilament PMC fabric yarn and coating the yarn with a coating having a composition which includes an additive for detecting a defect on the PMC fabric yarn and/or a PMC fabric formed by the PMC fabric yarn.

An advantage of the present invention is that defects such as contamination and/or imperfections or holes may quickly be detected and addressed in order to avoid sheet moisture profile unevenness, sheet instability, and the transfer of deposits from the PMC fabric to the paper.

Another advantage of the present invention is that the addition of the UV additive does not substantially alter the physical properties of the monofilament yarn.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1A:
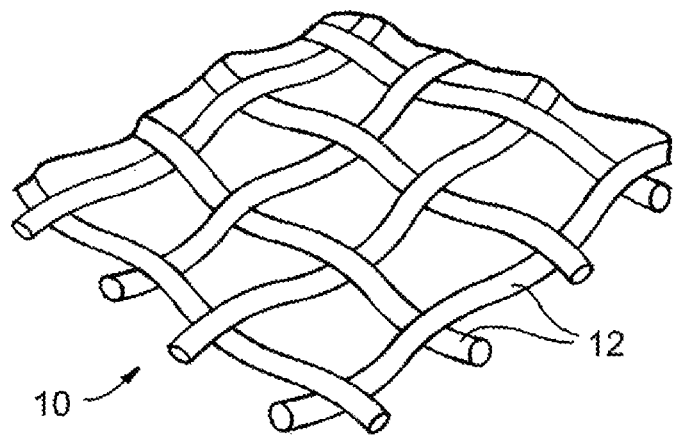
FIG. 1A is a fragmentary, perspective view of a portion of a fabric including an embodiment of a monofilament yarn according to the present invention.

Referring now to the drawings, and more particularly to FIG. 1A, there is shown a portion of an embodiment of a PMC fabric 10 including a plurality of woven monofilament yarns 12. The specific configuration of fabric 10 may vary, depending upon the application. For example, the specific weave pattern of fabric 10 may vary from one application to another. Moreover, fabric 10 need not necessarily be a woven fabric, but may include non-woven yarns 12.

The composition of the monofilament yarns includes an additive such as a UV additive, for example Eastobrite OB-1™ which is manufactured by Eastman Chemicals, and a thermoplastic resin. In order to monitor the cleanliness and the overall condition of the PMC fabric, a UV additive is added during the monofilament yarn making process. This additive makes the yarn easily visible in the presence, for example, of a black light (which generally emits radiation at wavelengths between approximately 350 nm and 390 nm) and enables quick detection of regions that do not contain UV additives, such as contamination or holes within the PMC fabric. A black light inspection process therefore makes the job easier for inspecting fabric for contaminants or damage during the cleaning process. The monofilament yarn with UV additive may also help the optical guiding mechanism for yarn and fabric.

Figure 1B:
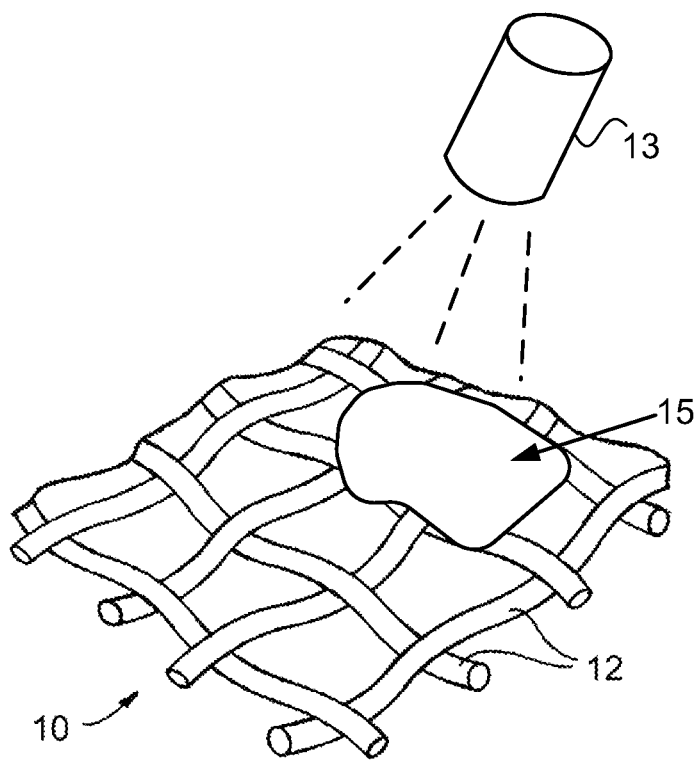
FIG. 1B is a fragmentary, perspective view of the portion of the PMC fabric of FIG. 1a including the monofilament yarn illustrating the visibility of contamination of or damage to the PMC fabric.

Referring now to FIG. 1B, PMC fabric 10 is formed from a plurality of monofilament yarns 12, for example woven yarns, including an additive loading of between approximately 100 to 10,000 parts per million (ppm), for example 1,000 ppm, which makes the yarn 12 easily visible under black light or radiation source 13 and allows for a contrast to be seen if non-UV additive containing areas 15 are present within the PMC fabric 10. These non-UV additive areas could include, but are not limited to, contamination and/or damaged areas within the fabric where the yarn is missing. The contrast created between the UV and non-UV additive areas allows for easy detection of fabric regions that could compromise the final paper quality.

Figure 2:
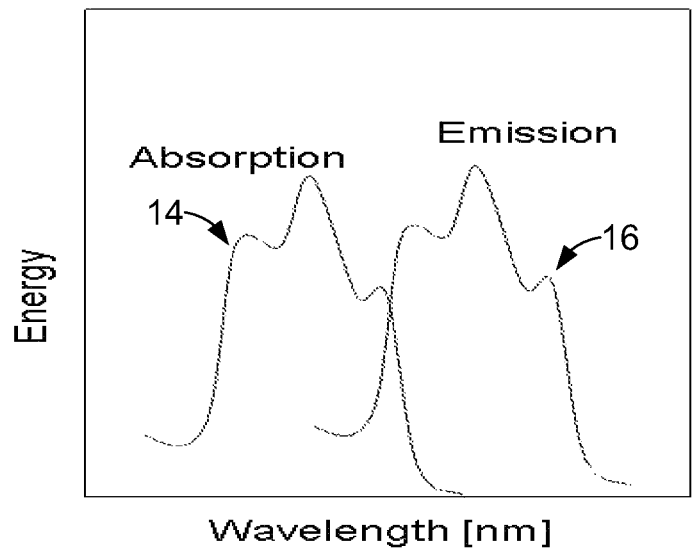
FIG. 2 is an illustration of absorption and emission spectra.

A UV additive, also known as an optical brightener (OB) or fluorescent whitening agent absorbs the short wavelength electromagnetic radiation from a radiation source 13, such as a black light having a wavelength e.g., between approximately 300 nm and 400 nm, which is invisible to the human eye and converts it into visible light of a longer wavelength, for example between approximately 400 nm and 500 nm, which is emitted either as violet, blue or greenish blue light. This principle is generally illustrated in FIG. 2, which illustrates absorption 14 and emission 16 spectra as they relate to energy and wavelength.

Figure 3:
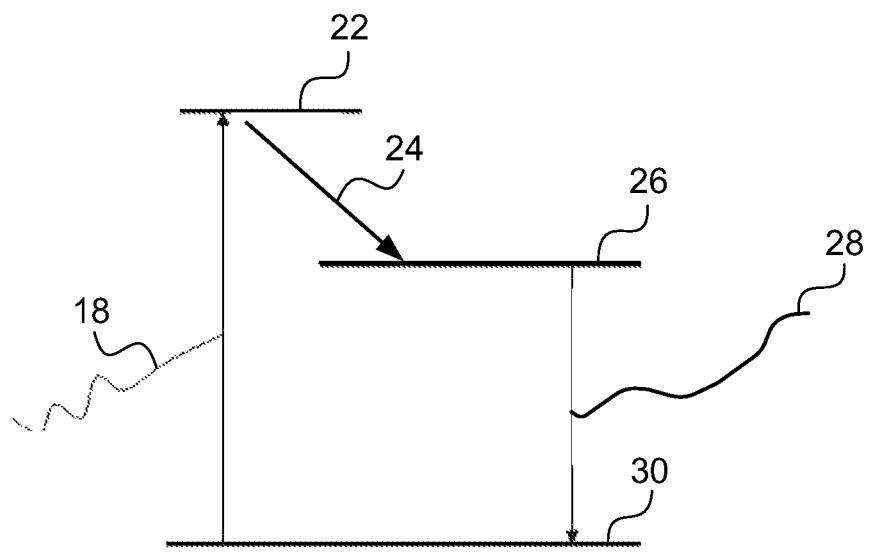
FIG. 3 is an illustration of the principle of fluorescence.

Fluorescent whitening agents are compounds that are excited or activated by wavelengths in the near-UV range, for example having a wavelength between approximately 360 nm and 365 nm, and then emit light in the blue range, for example having a wavelength between approximately 400 nm and 440 nm. Electrons in fluorescent molecules are excited into a higher energy state by absorption of light, which then emit a small amount of heat plus fluorescence as the electrons return to their ground state. FIG. 3 illustrates this general principle via the application of wavelengths of light 18 in the near-UV range, for example between approximately 360 nm and 365 nm, to a molecule of fluorescent whitening agent 20 which thereby activates the fluorescent whitening agent by exciting the electrons of the fluorescent molecules, raising the them to a higher energy state 22 by absorption of light 18, which then results in the emission of a small amount of heat 24 and a second lower excited state 26 plus fluorescence 28 as the electrons of the fluorescent molecules return to their ground state 30, which is the lowest energy state of the molecule.

Example 1

A sample PET monofilament yarn without a UV additive was compared with a PET monofilament yarn including a UV additive. Table 1 shows some of the physical properties of the PET monofilament used for a PMC Dryer Fabric. The control sample (with no UV additive) is shown in the first column and the properties of the yarn with the UV additive, 1000 ppm loading, are shown in the second column. Table 1 shows that the physical properties of the yarn with the UV additive are substantially the same as the PET monofilament without the UV additive. Therefore, it is clear that the UV additive according to the present invention does not substantially alter the physical characteristics of the monofilament yarn.

TABLE 1

PET Dryer Yarn Comparison (with and without UV Additive)

|  | PET 0.40 mm | With Additive PET 0.40 mm | PET 0.33 mm | With Additive PET 0.33 mm |
| --- | --- | --- | --- | --- |
| Denier (g/9000 m) | 1560 | 1565 | 1066 | 1060 |
| TEX (g/1000 m) | 173 | 174 | 118 | 118 |
| Tenacity (g/den) | 5.8 | 5.9 | 5.9 | 5.8 |
| Tenacity (cN/tex) | 51.2 | 52.1 | 52.1 | 51.2 |
| Modulus (g/den) | 75 | 75 | 79.4 | 80 |
| Modulus (cN/tex) | 662 | 662 | 701 | 706 |
| Elongation (%) | 17.7 | 17.8 | 18 | 17 |
| Loop Strength (lbs) | 15.5 | 15.6 | 11.4 | 11.1 |
| Loop Strength (N) | 69.0 | 69.5 | 50.8 | 49.4 |
| Knot Strength (lbs) | 9.4 | 9.2 | 7.7 | 7.8 |
| Knot Strength (N) | 41.9 | 41.0 | 34.3 | 34.7 |
| Shrink Force (g) | 317 | 320 | 203 | 200 |
| Shrink Force (cN/tex) | 1.79 | 1.80 | 1.68 | 1.67 |
| T@Max Shrink Force (C.) | 170 | 171 | 170 | 169 |
| Shrinkage (140 C., 3 min) (%) | 8.5 | 8.6 | 6.7 | 6.5 |

Figure 4:
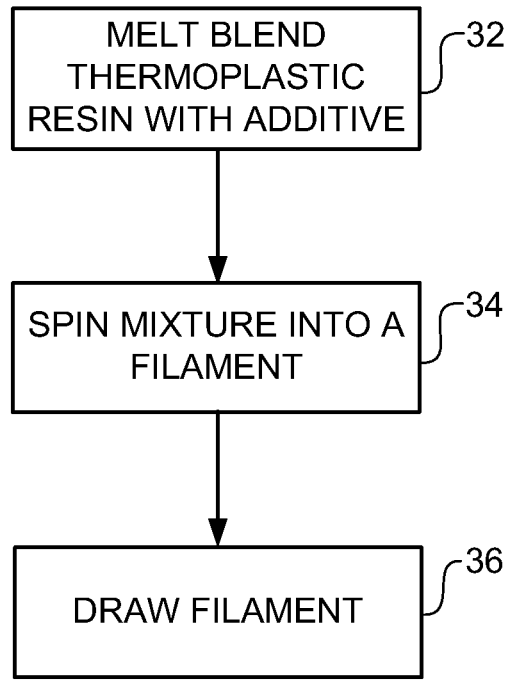
FIG. 4 is a flow chart illustrating an embodiment of the method of making monofilament yarns according to the present invention.

During the manufacture of PMC fabric 10, a screw extruder is used to melt blend thermoplastic resin and an additive, for example a stilbene. (FIG. 4, block 32). The mixture is then spun into a filament (block 34). The filament is then subsequently drawn into a monofilament PMC fabric yarn with at least one predetermined physical property (block 36).

Figure 5:
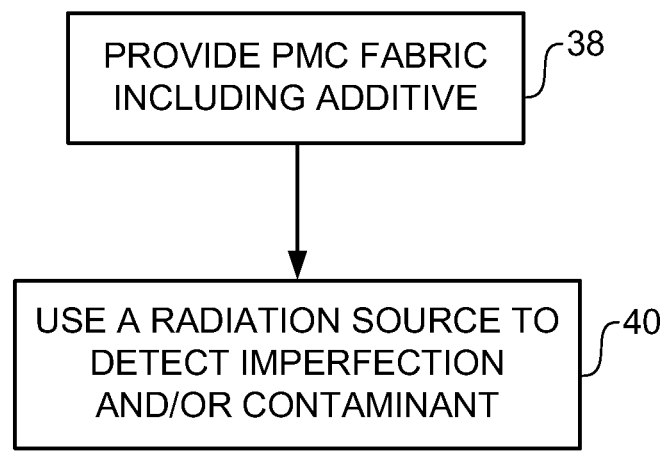
FIG. 5 is a flow chart illustrating an embodiment of the method of inspecting a paper machine clothing fabric according to the present invention.

During the inspection of a PMC fabric according to the present invention, a PMC fabric is provided which includes a plurality of monofilament yarns, at least some of which include between approximately 100 ppm and 10,000 ppm of a UV additive. (FIG. 5, block 38). A radiation source 13, such as a black light, emits short wavelength radiation, for example at a wavelength of between approximately 300 nm and 400 nm, to detect imperfections, damaged areas and/or contaminants on the PMC fabric. (block 40).

Figure 6:
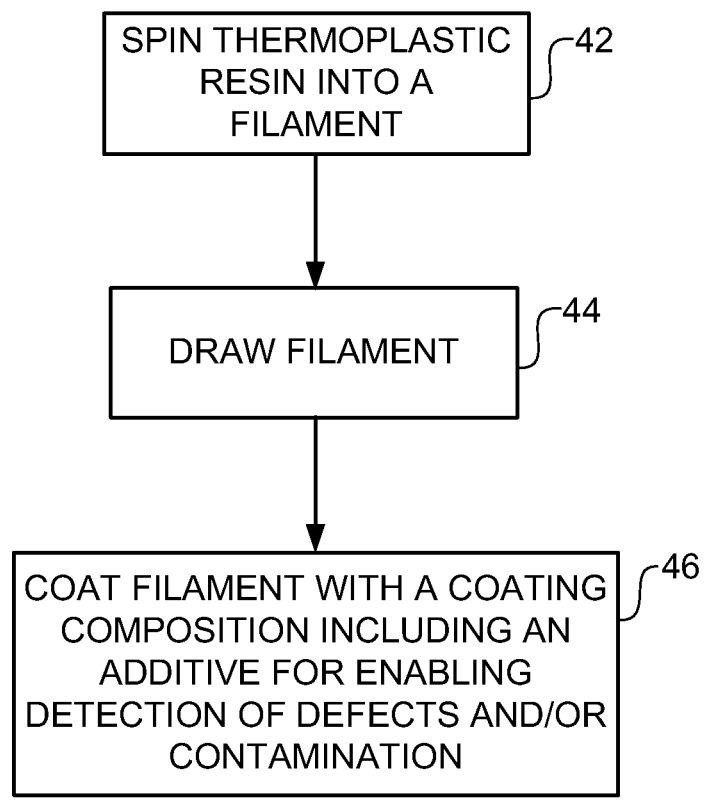
FIG. 6 is a flow chart illustrating an embodiment of the method of producing a PMC fabric yarn according to the present invention.

Referring now to FIG. 6, there is shown a flow diagram illustrating a method of manufacturing an embodiment of the PMC yarn according to the present invention. According to the method of the present invention, a thermoplastic resin is spun into a filament (block 42) and subsequently drawn (block 44). The drawn filament is then coated with a composition including an additive which enables the detection of defects and/or contaminants in the PMC fabric thread and/or a PMC fabric formed with the PMC fabric threads (block 46).

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A paper machine clothing (PMC) fabric including a plurality of monofilament yarns, at least some of said monofilament yarns having a composition which includes between approximately 100 and 10,000 parts per million (ppm) of an additive for detecting a defect on the PMC fabric using a light source, said additive being one of an ultra violet (UV) additive, an infrared (IR) additive and a metal powder additive.

2. The PMC fabric according to claim 1, wherein said UV additive is a stilbene.

3. The PMC fabric according to claim 2, wherein said stilbene is 4,4'-bis (benzoxazol) stilbene.

4. The PMC fabric according to claim 1, wherein at least some of said monofilament yarns include approximately 1,000 ppm loading of said UV additive.

5. The PMC fabric according to claim 1, wherein said defect on the PMC fabric is detectable using a short wavelength radiation at a wavelength of between approximately 300 nanometers (nm) and 400 nm.

6. The PMC fabric according to claim 1, wherein said defect is at least one of contamination and a damaged area of the PMC fabric.

7. The PMC fabric according to claim 1, wherein said composition further comprises a thermoplastic resin.

8. The PMC fabric according to claim 1, wherein said PMC fabric includes a plurality of woven yarns.

9. A paper machine clothing (PMC) fabric including a plurality of monofilament yarns, at least some of said monofilament yarns having a composition which includes between approximately 100 and 10,000 parts per million (ppm) of an ultraviolet (UV) additive for detecting a defect on the PMC fabric using short wavelength radiation at a wavelength of between approximately 300 nanometers (nm) and 400 nm.

10. The PMC fabric according to claim 9, wherein said composition includes approximately 1,000 ppm of said UV additive.

11. The PMC fabric according to claim 9, wherein said UV additive is a stilbene.

12. The PMC fabric according to claim 11, wherein said stilbene is 4,4'-bis (benzoxazol) stilbene.

13. The PMC fabric according to claim 9, wherein said defect is at least one of contamination and a damaged area of the PMC fabric.

14. The PMC fabric according to claim 9, wherein said composition further includes a thermoplastic resin.

* * * * *